US008309560B2

(12) United States Patent
Kil et al.

(10) Patent No.: US 8,309,560 B2
(45) Date of Patent: Nov. 13, 2012

(54) METHODS AND COMPOSITIONS FOR AMELIORATING THE UNDESIRABLE EFFECTS OF CHEMOTHERAPY

(75) Inventors: Jonathan Kil, Seattle, WA (US); Eric D. Lynch, Lake Forest Park, WA (US)

(73) Assignee: Sound Pharmaceuticals Incorporated, Seattle, WA (US)

( * ) Notice: Subject to any disclaimer, the term of this patent is extended or adjusted under 35 U.S.C. 154(b) by 0 days.

(21) Appl. No.: 12/946,694

(22) Filed: Nov. 15, 2010

(65) Prior Publication Data

US 2011/0065729 A1 Mar. 17, 2011

Related U.S. Application Data

(63) Continuation of application No. 11/299,084, filed on Dec. 9, 2005, now abandoned, which is a continuation of application No. 10/307,245, filed on Nov. 27, 2002, now abandoned.

(60) Provisional application No. 60/334,140, filed on Nov. 29, 2001.

(51) Int. Cl.
*A01N 43/90* (2006.01)
*A01N 43/64* (2006.01)
*A01N 37/12* (2006.01)
*A01N 37/44* (2006.01)
*A61K 31/519* (2006.01)
*A61K 31/41* (2006.01)
*A61K 31/195* (2006.01)

(52) U.S. Cl. ............... 514/262.1; 514/359; 514/562
(58) Field of Classification Search ............... 514/262.1, 514/359, 562
See application file for complete search history.

(56) References Cited

U.S. PATENT DOCUMENTS

| | | | |
|---|---|---|---|
| 4,352,799 A | 10/1982 | Renson | |
| 4,774,252 A | 9/1988 | Welter | |
| 5,385,726 A | 1/1995 | Baldew | |
| 5,795,909 A | 8/1998 | Shashoua | |
| 5,919,815 A | 7/1999 | Bradley | |
| 6,093,743 A | 7/2000 | Lai | |
| 6,177,434 B1 | 1/2001 | Kopke | |
| 6,601,580 B1 | 8/2003 | Bloch | |
| 6,815,434 B2 | 11/2004 | Kil | |
| 2003/0157191 A1 | 8/2003 | Kil | |
| 2004/0220145 A1 | 11/2004 | Kil | |
| 2005/0147978 A1 | 7/2005 | Remacle | |
| 2006/0089313 A1 | 4/2006 | Kil | |

FOREIGN PATENT DOCUMENTS

| | | |
|---|---|---|
| DE | 3638124 A1 | 5/1988 |
| DE | 198 56 210 A1 | 4/2000 |
| EP | 1 609 479 A1 | 12/2005 |
| WO | 92/02221 A1 | 2/1992 |
| WO | 01/80832 A2 | 11/2001 |
| WO | 03/045334 A2 | 6/2003 |
| WO | 2004/080486 A1 | 9/2004 |

OTHER PUBLICATIONS

Minami et. al. (Biological trace element research (1996) 55:1-7).*
Rybak et. al. (Annals of the New York Academy of Sciences, (1999) 884:143-151).*
Freireich et. al. (Cancer Chemotherapy (1966) 50:219-244).*
Attanasio, G., et al., "Effetto Prottetivo dell'Allopurinolo nell'Esposizione a Rumore Impulsivo," Acta Otorhinolaryngol Ital 19:6-11, 1999. [See English abstract.].
Baldew, G.S., et al., "The Influence of Ebselen on the Toxicity of Cisplatin in LLC-PK1 Cells," Biochemical Pharmacology 44(2):382-387, Jul. 22, 1992.
Baldew, G.S., et al., "Selective Reduction of cis-Diamminedichloroplatinum(II) Nephrotoxicity by Ebselen," Cancer Research 50:7031-7036, Nov. 1, 1990.
Coleman, J.K.M, et al., "Low Dose Methionine with N-Acetyl-L-Cysteine Reduces Noise-Induced Threshold Shift in the Chinchilla," ARO Abstract No. 861 25:226, Jan. 15, 2002.
Coleman, J.K.M., et al., "Post-Noise Administration of Methionine Attenuates Noise-Induced Hearing Loss in the Chinchilla," ARO Abstract No. 862-25:226, Jan. 15, 2002.
Cotgreave, I.A., and P. Moldéus, "Lung Protection by Thiol-Containing Antioxidants," Bulletin Européen de Physiopathologie Respiratoire 23(4):275-277, 1987.
Cotgreave, I.A., et al., "The Anti-Inflammatory Activity of Ebselen but Not Thiols in Experimental Alveolitis and Bronchiolitis," Agents and Actions 24(3/4):313-319, 1988.
Curti, B.D., "Physical Barriers to Drug Delivery in Tumors," Critical Reviews in Oncology/Hematology 14:29-39, 1993.
Cuzzocrea, S., "Beneficial Effects of n-acetylcysteine on Ischaemic Brain Injury," British Journal of Pharmacology 130(6):1219-1226, 2000.
Database WPI, Week 200468, Thomson Scientific, London, GB: AN 2004-699386 and WO 2004/080486 A, Sep. 23, 2004.
Dawson, D.A., et al., "The Neuroprotective Efficacy of Ebselen (a Glutathione Peroxidase Mimic) on Brain Damage Induced by Transient Focal Cerebral Ischaemia in the Rat," Neuroscience Letters 185(1):65-69, 1995.
Dehne, N., et al., "In Vitro Effects of Hydrogen Peroxide on the Cochlear Neurosensory Epithelium of the Guinea Pig," Hearing Research 143(1-2):162-170, May 2000.

(Continued)

*Primary Examiner* — Marcos Sznaidman
(74) *Attorney, Agent, or Firm* — Christensen O'Connor Johnson Kindness PLLC

(57) ABSTRACT

In one aspect, the present invention provides chemoprotectant compositions that each comprise at least two of the chemoprotectants disclosed herein. The chemoprotectant compositions of the invention are useful, for example, for ameliorating at least one adverse effect of chemotherapy. In another aspect, the present invention provides methods of ameliorating at least one adverse effect of chemotherapy, the methods each comprising the step of administering to a subject undergoing chemotherapy an amount of a chemoprotectant composition that is effective to ameliorate at least one adverse effect of the chemotherapy.

6 Claims, 6 Drawing Sheets

OTHER PUBLICATIONS

Doi, K, et al., "Radical Scavenger Edaravone Developed for Clinical Use Ameliorates Ischemia/Reperfusion Injury in Rat Kidney," Kidney International 65: 1714-1723, 2004.
Duan, M., et al. "Antioxidant N-L-Acetylcysteine (NAC) Can Protect Cochlea From Impulse Noise Trauma," ARO Abstract No. 860 25:226, Jan. 15, 2002.
Ekborn, A., et al., "Intracochlear Administration of Thiourea Protect Against Cisplatin Induced Ototoxicity in the Guinea Pig," ARO Abstract No. 854 25:224, Jan. 15, 2002.
Feghali, J.G., et al., "L-N-Acetyl-Cysteine Protection Against Cisplatin-Induced Auditory Neuronal and Hair Cell Toxicity," Laryngoscope 111(7):1147-1155, Jul. 2001.
Ferrer, J.V., et al., "Allopurinol and N Acetylcysteine Avoid 60% of Intestinal Necrosis in an Ischemia-Reperfusion Experimental Model," Transplantation Proceedings 30(6):2672, 1988.
Fischer, H., et al., "A Novel Biologically Active Selenoorganic Compound. VIII. Biotransformation of Ebselen," Xenobiotica 18(12):1347-1359, Dec. 1988.
Gillette Cloven, N., et al., "Evaluation of D-Methionine as a Cytoprotectant in Cisplatin Treatment of an Animal Model for Ovarian Cancer," Anticancer Research 20:4205-4209, Nov.-Dec. 2000.
Greenberg, B., et al., "Neoadjuvant Therapy for Advanced Head and Neck Cancer With Allopurinol-Modulated High Dose 5-Flourouracil and Cisplatin," Cancer 59(11):1860-1865, Jun. 1, 1987.
Gustafson, D.L., and C.A. Pritsos, "Inhibition of Mitomycin C's Aerobic Toxicity by the Seleno-Organic Antioxidant PZ-51," Cancer Chemotherapy and Pharmacology 28(3):228-230, 1991.
Herrick, A.L., et al., "A Double-Blind Placebo-Controlled Trial of Antioxidant Therapy in Limited Cutaneous Systemic Sclerosis," Clinical and Experimental Rheumatology 18(3):349-356, May-Jun. 2000.
Husain, K, et al., "Carboplatin-Induced Oxidative Stress in Rat Cochlea," Hearing Research 158:14-22, 2001.
Iwasaka, K., et al., "Role of Hydrogen Peroxide in Cytotoxicity Induction by Ascorbates and Other Redox Compounds," Anticancer Research 18:4333-4337, 1998.
Jain, R.K., "Barriers to Drug Delivery in Solid Tumors," Scientific American 271(1):58-65, Jul. 1994.
Johnson, J.I., et al., "Relationships Between Drug Activity in NCI Preclinical In Vitro and In Vivo Models and Early Clinical Trials," British Journal of Cancer 84(10):1424-1431, 2001.
Kalinec, G.M., et al., "Protective Role of L-Carnitine on the Ototoxic Effects of Cisplatin in Newborn Guinea Pigs," ARO Abstract No. 855 25:225, Jan. 15, 2002.
Kern, D.H., "Heterogeneity of Drug Resistance in Human Breast and Ovarian Cancers," Cancer Journal From Scientific American 4(1):41-45, 1998.
Kopke, R.D., et al., "Reduction of Noise-Induced Hearing Loss Using L-NAC and Salicylate in the Chinchilla," Hearing Research 149(1-2):138-146, Nov. 2000.
Kopke, R.D., et al., "Use of Organotypic Cultures of Corti's Organ to Study the Protective Effects of Antioxidant Molecules on Cisplatin-Induced Damage of Auditory Hair Cells," Amer. Journal of Otology 18:559-571, 1997.
Lautermann, J., et al., "Glutathione-Dependent Antioxidant Systems in the Mammalian Inner Ear: Effects of Aging, Ototoxic Drugs and Noise," Hearing Research 114:75-82, 1997.
Lopez-Gonzalez, M.A., "Ototoxicity Caused by Cisplatin Is Ameliorated by Melatonin and Other Antioxidants," Journal of Pineal Research 28(2):73-80, 2000.
Lynch, E.D., et al., "Combined Oral Delivery of Ebselen and Allopurinol Reduces Multiple Cisplatin Toxicities in Rat Breast and Ovarian Cancer Models While Enhancing Anti-Tumor Activity," Anti Cancer Drugs 16(5):569-579, 2005.
Lynch, E.D., et al., "Reduction of Acute Cisplatin Ototoxicity and Nephrotoxicity in Rats by Oral Administration of Allopurinol and Ebselen," Hearing Research 201(1-2):81-89, Mar. 2005.
Masumoto, H., et al., "Kinetic Study of the Reaction of Ebselen With Peroxynitrite," FEBS 398:179-182, 1996.

McFadden, S.L., et al., "M40403, a Superoxide Dismutase Mimetic, Protects Cochlear Hair Cells From Gentamicin, but Not Cisplatin Toxicity," Toxicology and Applied Pharmacology 186(1):46-54, Jan. 1, 2003.
Minami, T., et al., "Free Radical Scavengers Suppress the Accumulation of Platinum in the Cerebral Cortex," Biological Trace Element Research 55(1-2):1-7, Oct.-Nov. 1996.
Muldoon, L.L., et al., "Rescue From Enhanced Alkylator-Induced Cell Death With Low Molecular Weight Sulfur-Containing Chemoprotectants," Journal of Pharmacology and Experimental Therapeutics 296(3):797-805, 2001.
Nakamura, Y., et al., "Ebselen, a Glutathione Peroxidase Mimetic Seleno-organic Compound, As a Multifunctional Antioxidant," The Journal of Biological Chemistry 277(4):2687-2694, Jan. 25, 2002.
Neuwelt, E.A., et al., "Therapeutic Efficacy of Aortic Administration of N-Acetylcysteine as a Chemoprotectant Against Bone Marrow Toxicity After Intracarotid Administration of Alkylators, With or Without Glutathione Depletion in a Rat Model," Cancer Research 61:7868-7874, Nov. 1, 2001.
Ogawa, A., et al., "Ebselen in Acute Middle Cerebral Artery Occlusion: A Placebo-Controlled, Double-Blind Clinical Trial," Cerebrovascular Diseases 9(2):112-118, Mar.-Apr. 1999.
Palmer, C., et al., "Reduction of Perinatal Hypoxic-Ischemia Brain Damage with Allopurinol," Pediatric Research 27(4):332-336, 1990.
Pourbakht, A., et al., "Ebselen has a Protective Effect on Noise Induced Hearing Loss," ARO Abstract No. 858 25:225, Jan. 15, 2002.
Pritsos, C.A, et al., "PZ-51 (Ebselen) In Vivo Protection Against Adriamycin-Induced Mouse Cardiac and Hepatic Lipid Peroxidation and Toxicity," Biochemical Pharmacology 44(4):839-841, 1992.
Ravi, R., et al., "Mechanism of Cisplatin Ototoxicity: Antioxidant System," Pharmacology & Toxicology 76(6):386-394, Jun. 1995.
Ren, X. et al. "A Novel Glutathione Peroxidase Mimic with Antioxidant Activity," Archives of Biochemistry and Biophysics 387(2):250-256, Mar. 15, 2001.
Rose, G.S., et al., "Development and Characterization of a Clinically Useful Animal Model of Epithelial Ovarian Cancer in the Fischer 344 Rat," American Journal of Obstetrics and Gynecology 175(3):593-599, Sep. 1996.
Rybak, L.P., and S. Somani, "Ototoxicity: Amelioration by Protective Agents," Annals New York Academy of Sciences 884:143-151, 1999.
Rybak, L.P., et al., "Application of Antioxidants and Other Agents to Prevent Cisplatin Ototoxicity," Laryngoscope 109:1740-1744, Nov. 1999.
Rybak, L.P., et al., "Effect of Protective Agents Against Cisplatin Ototoxicity," American Journal of Otology 21(4): 513-520, 2000.
Sakagami, H., et al., "Induction of Non-Apoptotic Cell Death by Sodium 5,6-Benzylidene-L-Ascorbate in a Human Salivary Gland Tumor Cell Line," Anticancer Research 19:4045-4048, 1999.
Sawa, T., et al., "Tyrosine Nitration by Peroxynitrite Formed from Nitric Oxide and Superoxide Generated by Xanthine Oxidase," The Journal of Biological Chemistry 275(42):32467-32474, Oct. 20, 2000.
Scarpidis, U., et al., "Inhibition of the JNK/c-Jun Pathway Arrests Oxidative Stress Induced Apoptosis of Rat Auditory Neurons In Vitro," ARO Abstract No. 853 25:224, Jan. 15, 2002.
Seidman, M.D., et al., "The Protective Effects of Allopurinol and Superoxide Dismutase-Polyethylene Glycol on Ischemic and Reperfusion-Induced Cochlear Damage," Otolaryngology—Head and Neck Surgery 105(3):457-463, Sep. 1991.
Seidman, M.D., et al., "The Protective Effects of Allopurinol and Superoxide Dismutase on Noise-Induced Cochlear Damage," Otolaryngology—Head and Neck Surgery 109(6):1052-1056, Dec. 1993.
Sies, H., "Ebselen, a Selenoorganic Compound as Glutathione Peroxidase Mimic," Free Radical Biology & Medicine 14(3):313-323, 1993.
Sloan Stakleff, K.D., et al., "A Novel Early-Stage Orthotopic Model for Ovarian Cancer in the Fischer 344 Rat," International Journal of Gynecological Cancer 15(2):246-254, 2005.
Smith, J.A., et al., "An Evaluation of Cytotoxicity of the Taxane and Platinum Agents Combination Treatment in a Panel of Human Ovarian Carcinoma Cell Lines," Gynecologic Oncology 98:141-145, Apr. 2, 2005.

Sogut, S., et al., "In Vivo Evidence Suggesting a Role for Purine-Catabolizing Enzymes in the Pathogenesis of Cisplatin-Induced Nephrotoxicity in Rats and Effect of Erdosteine Against This Toxicity," Cell Biochemistry and Function 22(3):157-162, May-Jun. 2004.

Song, B.-B., and J. Schacht, "Variable Efficacy of Radical Scavengers and Iron Chelators to Attenuate Gentamicin Ototoxicity in Guinea Pig In Vivo," Human Research 94(1-2):87-93, 1996.

Suzuki, M., and M. Tsuchiya, "Ischemic Reperfusion Injury and Its Mechanism in Small Intestine," Journal of Clinical and Experimental Medicine (Igaku no Ayumi) 159(7):432, 1991. [English translation.].

Tsavaris, N.B., et al., "Decreased Oral Toxicity With the Local Use of Allopurinol in Patients Who Received High Dose 5-Fluorouracil," Selective Cancer Therapeutics 7(3):113-117, 1991.

Usui, M., et al., "Pathogenic Role of Oxidative Stress in Vascular Angiotensin-Converting Enzyme Activation in Long-Term Blockade of Nitric Oxide Synthesis in Rats," Hypertension 34:546-551, 1999.

Vermeulen, N.P.E., et al., "Toxicity of Fotemustine in Rat Hepatocytes and Mechanism-Based Protection Against it," Chemico-Biological Interactions 110(3):139-158, 1998.

Yamaguchi, T., et al., "Ebselen in Acute Ischemic Stroke: A Placebo-Controlled, Double-Blind Clinical Trial," Stroke 29:12-17, 1998.

Yoshida, M., et al., "Prevention of Nephrotoxicity of Cisplatin by Repeated Oral Administration of Ebselen in Rats," Tohuku J. Exp. Med. Abstract 191(4):209-220, 2000.

Zhou, Z.-B., et al., "Synthesis and Anti-Tumor Activity of Ebselen and Its Derivatives," Chemical Journal of Chinese Universities 14(2):220-222, 1993.

Physicians Desk Reference, 51st Ed., 1997, pp. 1194-1196.

"Cancer Multidrug Resistance," Nature Biotechnology 18(Supplement):IT18-IT20, 2000, reprinted from Nature Biotechnology 17:94-95, 1999.

Erdinç, M., et al., "Potentiation of Cisplatin-Induced Nephrotoxicity in Rats by Allopurinol," Experimental and Toxicologic Pathology 52(4):329-334, Aug. 2000.

* cited by examiner

METHODS AND COMPOSITIONS FOR AMELIORATING THE UNDESIRABLE EFFECTS OF CHEMOTHERAPY

CROSS-REFERENCES TO RELATED APPLICATIONS

This application is a continuation of application Ser. No. 11/299,084, filed Dec. 9, 2005, which is a continuation of application Ser. No. 10/307,245, filed Nov. 27, 2002, which claims the benefit of Provisional Application No. 60/334,140, filed Nov. 29, 2001.

FIELD OF THE INVENTION

The present invention relates to methods and compositions for ameliorating the undesirable effects of chemotherapy, such as chemotherapy that utilizes cisplatin.

BACKGROUND

One approach to the treatment of cancer is chemotherapy in which one or more chemical substances that are toxic, or otherwise deleterious, to the cancerous cells are administered to an individual suffering from cancer. Unfortunately, most, if not all, chemotherapeutic agents cause undesirable effects that adversely affect the health of the patient.

By way of example, the chemotherapeutic agent cisplatin (cis-diamminedichloroplatinum) is a heavy metal complex, with platinum as the central atom surrounded by two chloride atoms and two ammonia molecules in the cis position. Cisplatin produces interstrand and intrastrand crosslinkage in DNA of rapidly dividing cells, thus preventing DNA, RNA, and/or protein synthesis.

Cisplatin is typically used (often in combination with other chemotherapeutic agents, such as paclitaxel, cyclophosphomide, vinblastine, doxorubicin and bleomycin) to treat patients having metastatic testicular tumors, metastatic ovarian tumors, carcinoma of the endometrium, bladder, head, or neck. Unfortunately, cisplatin causes numerous adverse effects, such as seizures, peripheral neuropathies, ototoxicity, hearing loss, deafness, vertigo, dizziness, blurred vision, nausea, vomiting, anorexia, diarrhea, constipation, myelosuppression, thrombocytopenia, anemia, neutropenia, and nephrotoxicity.

Thus, there remains a need for compositions and methods that ameliorate or eliminate the undesirable effects of chemotherapy. In particular, there remains a need for compositions and methods that ameliorate or eliminate one or more, or all, of the undesirable effects of cisplatin chemotherapy.

SUMMARY

In one aspect, the present invention provides chemoprotectant compositions that each comprise at least two of the chemoprotectants disclosed herein. The chemoprotectant compositions of the invention are useful, for example, for ameliorating at least one adverse effect of chemotherapy.

In another aspect, the present invention provides pharmaceutical compositions that each include: (a) a chemoprotectant selected from the group consisting of methionine, N-acetyl-DL-methionine, S-adenosylmethionine, cysteine, homocysteine, cystathione, cysteamine, N-acetylcysteine, glutathione, glutathione ethylester, glutathione diethylester, glutathione triethylester, cysteamine, DiNAC, RibCys, RibCyst, β-LactCys, α-LactCys, MeliCys, MaltCys, CellCys, OTCA, allopurinol, 1-methylallopurinol, 2-methylallopurinol, 5-methylallopurinol, 7-methylallopurinol, 1,5-dimethylallopurinol, 2,5-dimethylallopurinol, 1,7-dimethylallopurinol, 2,7-dimethylallopurinol, 5,7-dimethylallopurinol, 2,5,7-trimethylallopurinol, 1-ethoxycarbonylallopurinol, 1-ethoxycarbonyl-5-methylallopurinol, 2-phenyl-1,2-benzoisoselenazol-3(2H)-one, and 6-diSeCD; and (b) a chemotherapeutic agent.

In another aspect, the present invention provides methods of ameliorating at least one adverse effect of chemotherapy, the methods each comprising the step of administering to a subject undergoing chemotherapy an amount of a chemoprotectant composition that is effective to ameliorate at least one adverse effect of the chemotherapy. The chemoprotectant composition comprises one or more (such as at least two) of the chemoprotectants disclosed herein.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
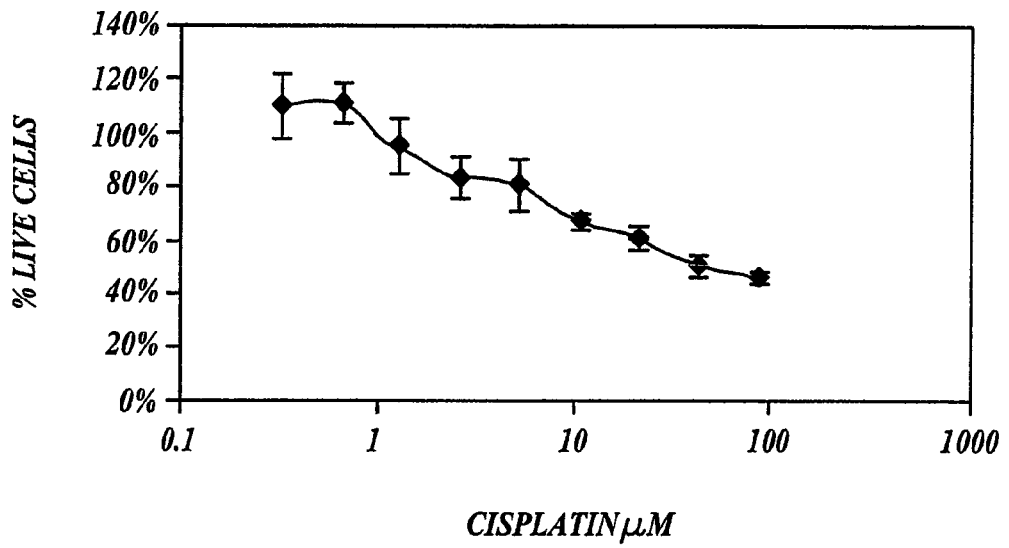
FIG. 1 shows a plot of the percentage of live, cultured, NuTu-19 ovarian cancer cells versus concentration of cisplatin in the culture medium. The number of live cells was measured after culturing the cells for 24 hours in the presence of cisplatin.

As used herein, the term "chemoprotectant" refers to a chemical substance that is capable of ameliorating at least one adverse effect of chemotherapy.

As used herein, the term "chemoprotectant composition" refers to a composition that includes at least one chemoprotectant, and may include more than one chemoprotectant. Chemoprotectant compositions may also include, in addition to one or more chemoprotectant(s), pharmaceutically acceptable carriers that facilitate administration of a chemoprotectant composition to a mammalian subject.

As used herein, the term "ameliorating at least one adverse effect of chemotherapy" includes: (a) reducing the magnitude and/or duration of at least one adverse effect of chemotherapy; and/or (b) completely eliminating at least one adverse effect of chemotherapy; and/or (c) preventing the onset of one or more adverse effect(s) of chemotherapy that would occur without administration of a chemoprotectant composition of the invention.

As used herein, the term "chemotherapeutic agent" is an agent that is administered to a mammalian subject to destroy, or otherwise adversely affect, cancer cells.

In one aspect the present invention provides methods for ameliorating at least one adverse effect of chemotherapy, the methods comprising the step of administering to a subject undergoing chemotherapy an amount of a chemoprotectant composition that is effective to ameliorate at least one adverse effect of the chemotherapy. The methods of the invention are applicable to any mammalian subject, such as a human subject, undergoing any form of chemotherapy.

The chemoprotectant compositions can include one or more than one chemoprotectant. Unless stated otherwise, any isomeric or tautomeric form of any of the chemoprotectants disclosed herein can be used in the invention. Some chemoprotectants that can be included in chemoprotectant compositions of the invention include one or more sulfur-containing groups (such as sulfhydryl or thiol groups). Representative examples of chemoprotectants that include one or more sulfur-containing groups are: methionine; N-acetyl-DL-methionine; S-adenosylmethionine; cysteine; homocysteine; cystathione; cysteamine; N-acetylcysteine; glutathione; glutathione ethylester; glutathione diethylester; glutathione triethylester; cysteamine; N,N'-diacetyl-L-cystine (DiNAC); 2(R,S)-D-ribo-(1',2'3',4'-tetrahydroxybutyl)-thiazolidine-4(R)-carboxylic acid (RibCys); 2-alkylthiazolidine 2(R,S)-D-ribo-(1',2',3',4'-tetrahydroxybutyl)thiazolidine (RibCyst); 2(R,S)-D-gluco-(1',2',4',5'-Tetrahydroxypentyl-3'-O-D-galactopyranosyl)thiazolidine-4(R)-carboxylic acid (β-LactCys); 2(R,S)-D-gluco-(1',2',4',5'-Tetrahydroxypentyl-3'-O-α-D-galactopyranosyl)thiazolidine-4(R)-carboxylic acid (α-LactCys); 2(R,S)-D-gluco-(1',2',3',4'-Tetrahydroxypentyl-5'-O-α-D-galactopyranosyl)thiazolidine-4(R)-carboxylic acid (MeliCys); 2(R,S)-D-gluco-(1',2',4',5'-Tetrahydroxypentyl-3'-O-α-D-glucopyranosyl)thiazolidine-4(R)-carboxylic acid (MaltCys); 2(R,S)-D-gluco-(1',2',4',5'-Tetrahydroxypentyl-3'-O-β-D-glucopyranosyl) thiazolidine-4(R)-carboxylic acid (CellCys); and 2-oxo-L-thiazolidine-4-carboxylic acid (OTCA).

Allopurinol ($C_5H_4N_4O$) and its tautomers are also useful as chemoprotectants in the practice of the invention. The following representative allopurinol derivatives are useful as chemoprotectants in the practice of the invention: 1-methylallopurinol; 2-methylallopurinol; 5-methylallopurinol; 7-methylallopurinol; 1,5-dimethylallopurinol; 2,5-dimethylallopurinol; 1,7-dimethylallopurinol; 2,7-dimethylallopurinol; 5,7-dimethylallopurinol; 2,5,7-trimethylallopurinol; 1-ethoxycarbonylallopurinol; and 1-ethoxycarbonyl-5-methylallopurinol.

Other examples of chemoprotectants useful in the practice of the invention include: 2-phenyl-1,2-benzoisoselenazol-3(2H)-one (Ebselen), and 6A,6B-diseleninic acid-6A',6B'-selenium bridged β-cyclodextrin (6-diSeCD).

Table 1 sets forth representative effective dosage ranges for some of the chemoprotectants described herein. The chemoprotectants set forth in Table 1 are preferably administered orally or intravenously. The chemoprotectants set forth in Table 1 can be administered to a mammalian subject before, during or after administration of one or more chemotherapeutic agents to the mammalian subject. Thus, a mammalian subject typically receives one dose of chemoprotectant(s) for each dose of chemotherapeutic agent(s).

In some embodiments of the invention, one or more of the chemoprotectants set forth in Table 1 are administered to a mammalian subject at any time during a period extending from 18 hours before administration of one or more chemotherapeutic agents to the mammalian subject, to 18 hours after administration of one or more chemotherapeutic agents to the mammalian subject. In some embodiments of the invention, one or more of the chemoprotectants set forth in Table 1 are administered to a mammalian subject at any time during a period extending from one hour before administration of one or more chemotherapeutic agents to the mammalian subject, to one hour after administration of one or more chemotherapeutic agents to the mammalian subject. In some embodiments of the invention, one or more of the chemoprotectants set forth in Table 1 are administered to a mammalian subject at any time during a period extending from 10 minutes before administration of one or more chemotherapeutic agents to the mammalian subject, to ten minutes after administration of one or more chemotherapeutic agents to the mammalian subject. In some embodiments of the invention, one or more of the chemoprotectants set forth in Table 1 are administered to a mammalian subject concurrently with administration of one or more chemotherapeutic agents to the mammalian subject.

The abbreviation "mg" means milligrams.

TABLE 1

| Compound(s) | Chemical name | Presently preferred range | Presently more preferred range | Presently most preferred range |
|---|---|---|---|---|
| NAM | N-acetyl-Methionine | 5-5000 mg/day | 50-2000 mg/day | 500-1000 mg/day |
| Methionine | Methionine | 5-5000 mg/day | 50-2000 mg/day | 500-1000 mg/day |
| SAM | S-adenosyl-Methionine | 5-5000 mg/day | 50-2000 mg/day | 500-1000 mg/day |
| Cysteine | Cysteine | 5-5000 mg/day | 50-2000 mg/day | 500-1000 mg/day |
| NAC | N-acetyl-L-Cysteine | 5-5000 mg/day | 50-2000 mg/day | 500-1000 mg/day |
| DiNAC | N,N'-diacetyl-cystine | 5-5000 mg/day | 50-2000 mg/day | 500-1000 mg/day |
| homocysteine | homocysteine | 5-5000 mg/day | 50-2000 mg/day | 500-1000 mg/day |
| RibCyst | 2-alkylthiazolidine, 2(R,S)-D-ribo-(1',2',3',4'-tetrahydroxybutyl)thiazolidine | 5-5000 mg/day | 50-2000 mg/day | 500-1000 mg/day |
| RibCys | 2(R,S)-D-ribo-(1',2'3',4'-tetrahydroxybutyl)-thiazolidine-4 (R)-carboxylic acid | 5-5000 mg/day | 50-2000 mg/day | 500-1000 mg/day |
| Cystathione | Cystathione | 5-5000 mg/day | 50-2000 mg/day | 500-1000 mg/day |
| Glutathione | Glutathione | 5-5000 mg/day | 50-2000 mg/day | 500-1000 mg/day |
| Glutathione ethyl ester | Glutathione ethyl ester | 5-5000 mg/day | 50-2000 mg/day | 500-1000 mg/day |
| Glutathione diethyl ester | Glutathione diethyl ester | 5-5000 mg/day | 50-2000 mg/day | 500-1000 mg/day |
| Glutathione triethyl ester | S-(1,2-dicarboxyethyl)glutathione triester | 5-5000 mg/day | 50-2000 mg/day | 500-1000 mg/day |
| Cysteamine | Cysteamine | 5-5000 mg/day | 50-2000 mg/day | 500-1000 mg/day |
| OTCA | 2-oxo-L-thiazolidine-4-carboxylic acid | 5-5000 mg/day | 50-2000 mg/day | 500-1000 mg/day |
| Allopurinol | 4-hydroxypyrazolo[3,4-d]pyrimidine | 10-2400 mg/day | 50-1200 mg/day | 100-800 mg/day |
| Ebselen | 2-phenyl-1,2-benzoisoselenazol-3 (2H)-one | 5-5000 mg/day | 50-2000 mg/day | 500-1000 mg/day |
| 6-diSeCD | 6A,6B-diseleninic acid-6A',6B'-selenium bridged beta-cyclodextrin | 5-5000 mg/day | 50-2000 mg/day | 500-1000 mg/day |

The chemoprotectant compositions can include one, or more than one, chemoprotectant(s). Thus, chemoprotectant compositions of the invention can include any combination of any of the individual chemoprotectants described herein. In some embodiments of the chemoprotectant compositions that include more than one chemoprotectant, the chemoprotectant compositions are formulated to provide an effective dosage of the individual constituent chemoprotectants as set forth in Table 1. For example, as set forth in Table 1, the presently preferred dosage of both methionine and N-acetyl-methionine is from 5 mg to 5000 mg per day. Accordingly, some chemoprotectant compositions of the invention are formulated to provide methionine and N-acetyl-methionine each at a dosage of from 5 mg to 5000 mg per day.

In another aspect, the present invention provides chemoprotectant compositions that each comprise at least two (e.g., two, three, four, five, six, seven, eight, nine or ten) of the individual chemoprotectants disclosed herein. For example, some chemoprotectant compositions include at least one chemoprotectant selected from Group A, at least one chemoprotectant selected from Group B, and at least one chemoprotectant selected from Group C, wherein Groups A, B and C include the following chemoprotectants:

Group A (glutathione or a glutathione precursor): methionine; N-acetyl-DL-methionine; S-adenosylmethionine; cysteine; N-acetylcysteine; glutathione; glutathione ethylester; glutathione diethylester; glutathione triethylester; DiNAC; RibCys; homocysteine; cystathione; cysteamine; OTCA and RibCyst.

Group B (strong antioxidants): allopurinol; 1-methylallopurinol; 2-methylallopurinol; 5-methylallopurinol; 7-methylallopurinol; 1,5-dimethylallopurinol; 2,5-dimethylallopurinol; 1,7-dimethylallopurinol; 2,7-dimethylallopurinol; 5,7-dimethylallopurinol; 2,5,7-trimethylallopurinol; 1-ethoxycarbonylallopurinol; and 1-ethoxycarbonyl-5-methylallopurinol.

Group C (Glutathione peroxidase mimic): Ebselen and 6-diSeCD.

The chemoprotectant compositions of the invention are useful, for example, for ameliorating at least one adverse effect of chemotherapy. The chemoprotectant compositions of the invention can be used in the methods of the invention for ameliorating at least one adverse effect of chemotherapy.

The chemoprotectant compositions of the invention can be formulated to provide a dosage that is effective to ameliorate one or more adverse effect(s) of chemotherapy when administered to a subject undergoing chemotherapy. For example, in some embodiments the chemoprotectant compositions are formulated to provide an effective dosage of the individual chemoprotectants as set forth in Table 1.

Administration of the chemoprotectant compositions of the invention is accomplished by any effective route, e.g., orally or parenterally. Methods of parenteral delivery include topical, intra-arterial, subcutaneous, intramedullary, intravenous, or intranasal administration. In addition to one or more chemoprotectants, the chemoprotectant compositions may contain suitable pharmaceutically acceptable carriers comprising excipients and other compounds that facilitate administration of the chemoprotectant compositions to a mammalian subject undergoing chemotherapy. Further details on techniques for formulation and administration may be found in the latest edition of "Remington's Pharmaceutical Sciences" (Maack Publishing Co, Easton, Pa.).

Chemoprotectant compositions for oral administration can be formulated using pharmaceutically acceptable carriers well known in the art, in dosages suitable for oral administration. Such carriers enable the chemoprotectant compositions to be formulated as tablets, pills, dragees, capsules, liquids, gels, syrups, slurries, suspensions, etc., suitable for ingestion by a subject.

Chemoprotectant compositions for oral use can be obtained, for example, through combination of one or more chemoprotectants with solid excipient, optionally grinding the resulting mixture, and processing the mixture of granules, after adding suitable additional compounds, if desired, to obtain tablets or dragee cores. Suitable excipients are carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilising agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound (i.e., dosage).

Chemoprotectant compositions, which can be used orally, can be formulated, for example, as push-fit capsules made of gelatin, as well as soft, sealed capsules made of gelatin and a coating such as glycerol or sorbitol. Push-fit capsules can contain chemoprotectants mixed with filler or binders such as lactose or starches, lubricants such as talc or magnesium stearate, and, optionally, stabilisers. In soft capsules, the chemoprotectant(s) may be dissolved or suspended in suitable liquids, such as fatty oils, liquid paraffin, or liquid polyethylene glycol with or without stabilisers.

Chemoprotectant compositions for parenteral administration include aqueous solutions of one or more chemoprotectants. For injection, the chemoprotectant compositions of the invention may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of chemoprotectants may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilisers or agents, which increase the solubility of the compounds to allow for the preparation of highly concentrated solutions.

For topical or nasal administration, penetrants appropriate to the particular barrier to be permeated are typically used in the formulation. Such penetrants are generally known in the art.

The chemoprotectant compositions of the present invention may be manufactured in a manner similar to that known in the art (e.g., by means of conventional mixing, dissolving, granulating, dragee-making, levigating, emulsifying, encapsulating, entrapping or lyophilising processes). The chemoprotectant compositions may also be modified to provide appropriate release characteristics, e.g., sustained release or targeted release, by conventional means (e.g., coating).

The chemoprotectant compositions may be provided as a salt and can be formed with many acids, including but not limited to hydrochloric, sulfuric, acetic, lactic, tartaric, malic, succinic, etc. Salts tend to be more soluble in aqueous or other protonic solvents than are the corresponding free base forms.

After such chemoprotectant compositions formulated in an acceptable carrier have been prepared, they can be placed in an appropriate container and labeled for use.

The amount actually administered will be dependent upon the individual to which treatment is to be applied, and will preferably be an optimized amount such that the desired effect is achieved without significant side-effects. The determination of an effective dose is well within the capability of those skilled in the art. Of course, the skilled person will realize that divided and partial doses are also within the scope of the invention.

For any chemoprotectant composition, the effective dose can be estimated initially either in cell culture assays or in any appropriate animal model (e.g., primate, rats and guinea pigs and other small laboratory animals). The animal model is also typically used to achieve a desirable concentration range and route of administration. Such information can then be used to determine useful doses and routes for administration in humans or other mammals.

Therapeutic efficacy and possible toxicity of chemoprotectant compositions can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $ED_{50}/LD_{50}$. Chemoprotectant compositions, which exhibit large therapeutic indices, are preferred. The data obtained from cell culture assays and animal studies is used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration.

In another aspect, the present invention provides pharmaceutical compositions that each include: (a) a chemoprotectant selected from the group consisting of methionine, N-acetyl-DL-methionine, S-adenosylmethionine, cysteine, homocysteine, cystathione, cysteamine, N-acetylcysteine, glutathione, glutathione ethylester, glutathione diethylester, glutathione triethylester, cysteamine, DiNAC, RibCys, RibCyst, β-LactCys, α-LactCys, MeliCys, MaltCys, CellCys, OTCA, allopurinol, 1-methylallopurinol, 2-methylallopurinol, 5-methylallopurinol, 7-methylallopurinol, 1,5-dimethylallopurinol, 2,5-dimethylallopurinol, 1,7-dimethylallopurinol, 2,7-dimethylallopurinol, 5,7-dimethylallopurinol, 2,5,7-trimethylallopurinol, 1-ethoxycarbonylallopurinol, 1-ethoxycarbonyl-5-methylallopurinol, 2-phenyl-1,2-benzoisoselenazol-3(2H)-one, and 6-diSeCD; and (b) a chemotherapeutic agent.

Examples of chemotherapeutic agents useful in the pharmaceutical compositions of the invention include cisplatin, carboplatin, oxaliplatin, vinblastine, doxorubicin, bleomycin, paclitaxel, cyclophosphomide, adriamycin, altretamine, methotrexate, and fluorouracil. In some embodiments, the chemotherapeutic agent includes platinum. Examples of chemotherapeutic agents that include platinum are cisplatin, carboplatin and oxaliplatin. The pharmaceutical compositions are blended to provide a dose of one or more chemotherapeutic agents that is/are effective to kill, or otherwise adversely affect, cancer cells. The pharmaceutical compositions are also blended to provide a dose of one or more chemoprotectants effective to ameliorate at least one undesirable effect of the chemotherapeutic agent(s). Examples of desired daily doses of each of the foregoing chemoprotectants are set forth in Table 1. An example of a daily dosage of cisplatin is administration once per week at 50-200 mg/meter$^2$ per dose with 4 to 6 weeks of chemotherapy. The pharmaceutical compositions of the invention have the advantage that they simultaneously provide the recipient with a dosage of one or more chemotherapeutic agents, and a dosage of one or more chemoprotectants.

The chemoprotectant compositions, pharmaceutical compositions, and methods of the present invention can be used to ameliorate any adverse effect of chemotherapy utilizing any chemotherapeutic agent. Some chemoprotectant compositions, and pharmaceutical compositions, of the invention ameliorate most or all of the adverse effects of chemotherapy when used in accordance with the present invention. By way of example, the compositions and methods of the present invention can be used to ameliorate one, some, or all of the adverse effects of any of the following chemotherapeutic agents: cisplatin, carboplatin, oxaliplatin, vinblastine, doxorubicin, bleomycin, paclitaxel, cyclophosphomide, adriamycin, altretamine, methotrexate, and fluorouracil. The principal adverse effects of the foregoing chemotherapeutic agents are: nephrotoxicity, neurotoxicity, ototoxicity, myelosuppression, alopecia, weight loss, vomiting, nausea and immunosuppression. The most effective chemoprotectant composition(s) of the invention for ameliorating one or more adverse effects of a specific chemotherapeutic agent can be readily determined by routine experimentation by one of ordinary skill in the art.

The following examples merely illustrate the best mode now contemplated for practicing the invention, but should not be construed to limit the invention. All literature citations herein are expressly incorporated by reference.

EXAMPLE 1

This example shows that N-acetylcysteine, Ebselen and allopurinol, alone, or in combination, do not inhibit the ability of cisplatin to kill cultured NuTu-19 ovarian cancer tumor cells as measured using the MTS cell viability assay.

NuTu-19 cells were plated at a density of 3,000 cells per well in 96 well culture dishes, and incubated at 37° C., in the presence of 5% carbon dioxide, for 24 hours. N-acetylcysteine, Ebselen or allopurinol were incubated for one hour, or for four hours, with the NuTu-19 cells, then cisplatin was added to the cultures which were further incubated at 37° C., in the presence of 5% carbon dioxide, for 24 hours. The NuTu-19 cells were then rinsed with media and incubated in the presence of cisplatin for an additional 24 hours.

The NuTu-19 cells were then rinsed twice with phosphate buffered saline (PBS), then MTS assays were performed to measure the number of living cells. MTS is an abbreviation for (3-(4,5-dimethylthiazol-2-yl)-5-(3-carboxymethoxyphenyl)-2-(4-sulfophenyl)-2H-tetrazolium. The MTS assay is a colorimetric method for determining the number of viable cells based upon physiologic catabolism of MTS to a formazan product that is soluble in tissue culture medium. The absorbance of the formazan product at 490 nm can be measured directly from a 96 well plate using a plate reader. Increased absorbance at 490 nm correlates with increased production of formazan in a well. This is typically due to more viable cells present in a well.

FIG. 1 shows a plot of the percentage of live, cultured, NuTu-19 ovarian cancer cells versus concentration of cisplatin in the culture medium. The data set forth in FIG. 1 show that cultured NuTu-19 ovarian cancer cells are killed after incubation for 24 hours in the presence of cisplatin.

Figure 2:
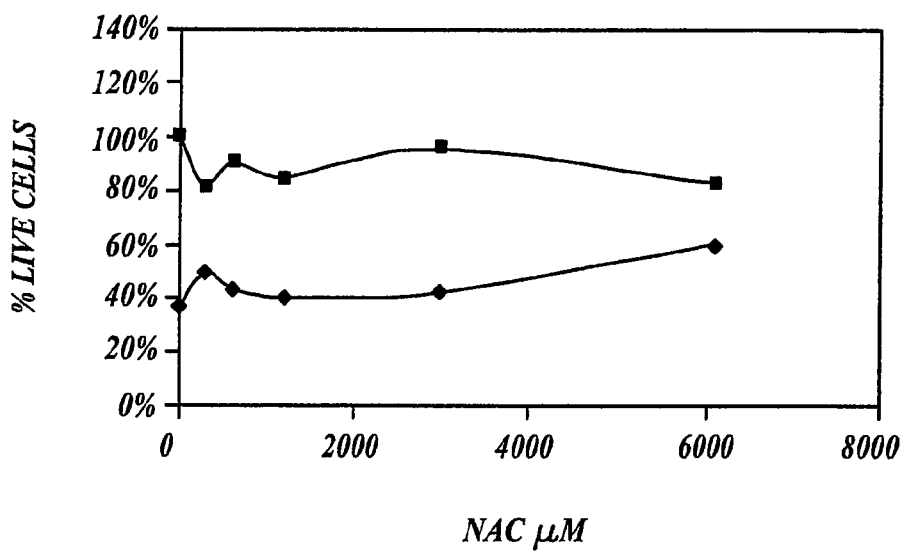
FIG. 2 shows a plot of the percentage of live, cultured, NuTu-19 ovarian cancer cells versus the concentration (in units of μM) of N-acetyl-cysteine (NAC) in the culture medium. The viability of NuTu-19 cells cultured in the presence of N-acetylcysteine, but not in the presence of cisplatin, is shown by the upper graph. The viability of NuTu-19 cells cultured in the presence of both N-acetylcysteine and cisplatin (at a concentration of 43 μM) is shown by the lower graph.

FIG. 2 shows a plot of the percentage of live, cultured, NuTu-19 ovarian cancer cells versus the concentration of N-acetylcysteine in the culture medium. The viability of NuTu-19 cells cultured in the presence of N-acetylcysteine, but not in the presence of cisplatin, is shown by the upper graph. The viability of NuTu-19 cells cultured in the presence of both N-acetylcysteine and cisplatin (at a concentration of 43 μM) is shown by the lower graph. The data set forth in FIG. 2 shows that N-acetylcysteine does not inhibit the ability of cisplatin to kill NuTu-19 ovarian cancer tumor cells in culture.

Figure 3:
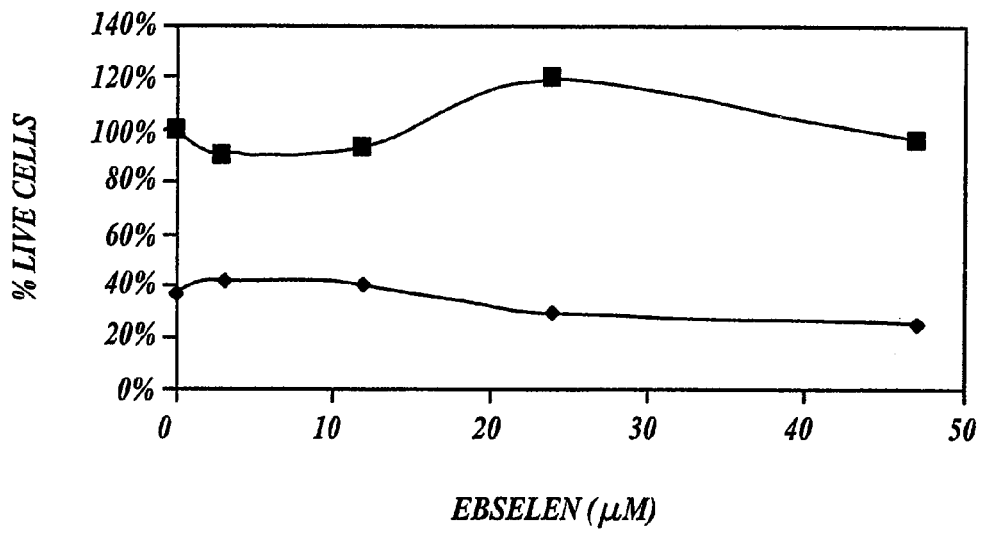
FIG. 3 shows a plot of the percentage of live, cultured, NuTu-19 ovarian cancer cells versus the concentration of Ebselen in the culture medium. The viability of NuTu-19 cells cultured in the presence of Ebselen, but not in the presence of cisplatin, is shown by the upper graph. The viability of NuTu-19 cells cultured in the presence of both Ebselen and cisplatin (at a concentration of 43 μM) is shown by the lower graph.

FIG. 3 shows a plot of the percentage of live, cultured, NuTu-19 ovarian cancer cells versus the concentration of Ebselen in the culture medium. The viability of NuTu-19 cells cultured in the presence of Ebselen, but not in the presence of cisplatin, is shown by the upper graph. The viability of NuTu-19 cells cultured in the presence of both Ebselen and cisplatin (at a concentration of 43 μM) is shown by the lower graph. The data set forth in FIG. 3 shows that Ebselen does not inhibit the ability of cisplatin to kill NuTu-19 ovarian cancer tumor cells in culture.

Figure 4:
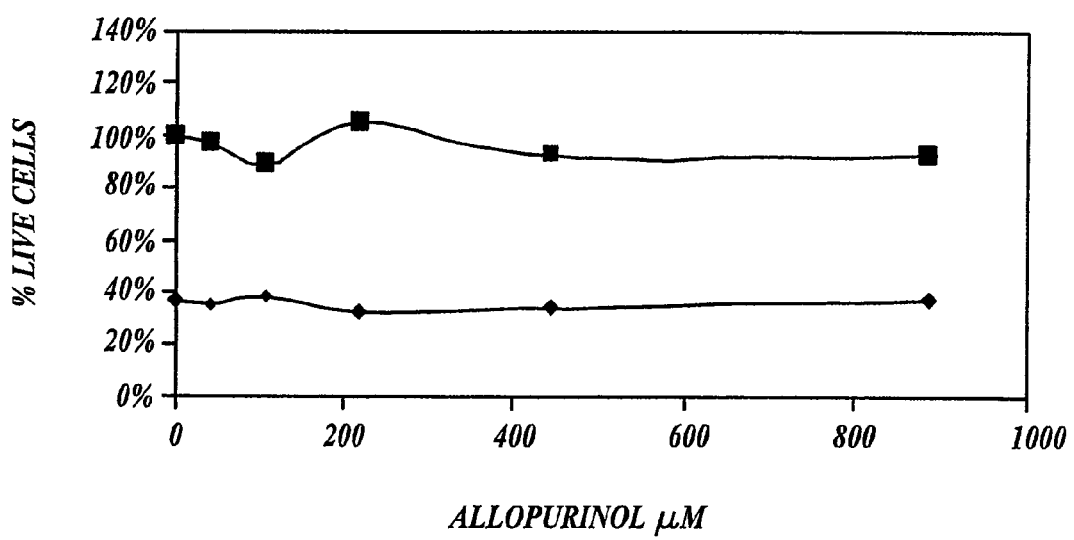
FIG. 4 shows a plot of the percentage of live, cultured, NuTu-19 ovarian cancer cells versus the concentration of allopurinol in the culture medium. The viability of NuTu-19 cells cultured in the presence of allopurinol, but not in the presence of cisplatin, is shown by the upper graph. The viability of NuTu-19 cells cultured in the presence of both allopurinol and cisplatin (at a concentration of 43 μM) is shown by the lower graph.

FIG. 4 shows a plot of the percentage of live, cultured, NuTu-19 ovarian cancer cells versus the concentration of allopurinol in the culture medium. The viability of NuTu-19 cells cultured in the presence of allopurinol, but not in the presence of cisplatin, is shown by the upper graph. The viability of NuTu-19 cells cultured in the presence of both allopurinol and cisplatin (at a concentration of 43 μM) is shown by the lower graph. The data set forth in FIG. 4 shows that allopurinol does not inhibit the ability of cisplatin to kill NuTu-19 ovarian cancer tumor cells in culture.

Figure 5:
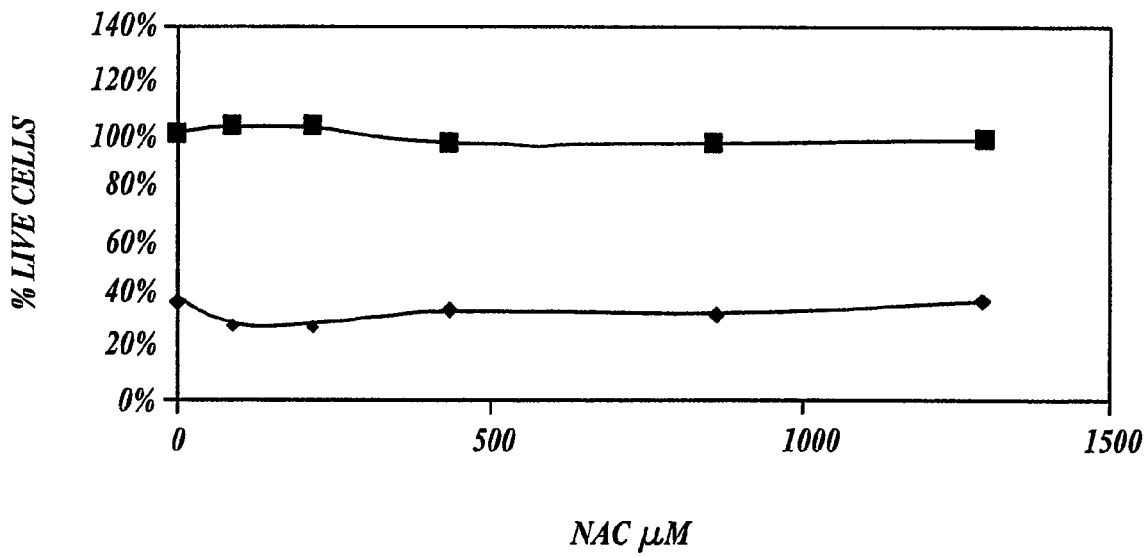
FIG. 5 shows a plot of the percentage of live, cultured, NuTu-19 ovarian cancer cells versus the concentration of N-acetylcysteine in the culture medium. The viability of NuTu-19 cells cultured in the presence of N-acetylcysteine and Ebselen (at a concentration of 47 μM), but not in the presence of cisplatin, is shown by the upper graph. The viability of NuTu-19 cells cultured in the presence of N-acetylcysteine, Ebselen (at a concentration of 47 μM) and cisplatin (at a concentration of 43 μM) is shown by the lower graph.

FIG. 5 shows a plot of the percentage of live, cultured, NuTu-19 ovarian cancer cells versus the concentration of N-acetyl-cysteine in the culture medium. The viability of NuTu-19 cells cultured in the presence of N-acetyl-cysteine and Ebselen (at a concentration of 47 μM), but not in the presence of cisplatin, is shown by the upper graph. The viability of NuTu-19 cells cultured in the presence of N-acetyl-cysteine, Ebselen (at a concentration of 47 μM) and cisplatin (at a concentration of 43 μM) is shown by the lower graph. The data set forth in FIG. 5 shows that the combination of N-acetyl-cysteine and Ebselen does not inhibit the ability of cisplatin to kill NuTu-19 ovarian cancer tumor cells in culture.

Figure 6:
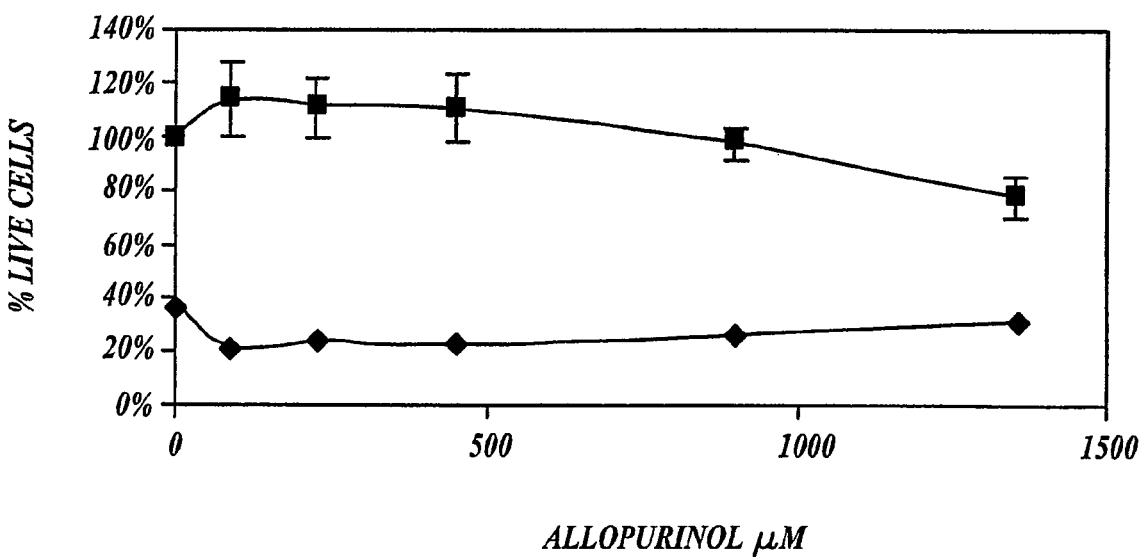
FIG. 6 shows a plot of the percentage of live, cultured, NuTu-19 ovarian cancer cells versus the concentration of allopurinol in the culture medium. The viability of NuTu-19 cells cultured in the presence of allopurinol and Ebselen (at a concentration of 47 μM), but not in the presence of cisplatin, is shown by the upper graph. The viability of NuTu-19 cells cultured in the presence of allopurinol and Ebselen (at a concentration of 47 µM) and cisplatin (at a concentration of 43 µM) is shown by the lower graph.

FIG. 6 shows a plot of the percentage of live, cultured, NuTu-19 ovarian cancer cells versus the concentration of allopurinol in the culture medium. The viability of NuTu-19 cells cultured in the presence of allopurinol and Ebselen (at a concentration of 47 μM), but not in the presence of cisplatin, is shown by the upper graph. The viability of NuTu-19 cells cultured in the presence of allopurinol and Ebselen (at a concentration of 47 μM) and cisplatin (at a concentration of 43 μM) is shown by the lower graph. The data set forth in FIG. 6 shows that the combination of allopurinol and Ebselen does not inhibit the ability of cisplatin to kill NuTu-19 ovarian cancer tumor cells in culture.

EXAMPLE 2

This Example shows that Ebselen protects inner ear hair cells from damage by cisplatin in vitro.

Three cochlea per treatment, obtained from P3-4 mouse pups, were cultured in 0.4 micrometer MilliCell-CM inserts with NeuroBasal A medium plus B27 supplement. After 24 hours in culture Ebselen was added to the medium, incubated for ten minutes, and then cisplatin was added to the medium at a final concentration of 43 μM. A first control treatment included 43 μM cisplatin. A second control treatment included 47 µM Ebselen without the addition of cisplatin. All cultures were incubated for 24 hours at 37° C. in 5% carbon dioxide.

Figure 7:
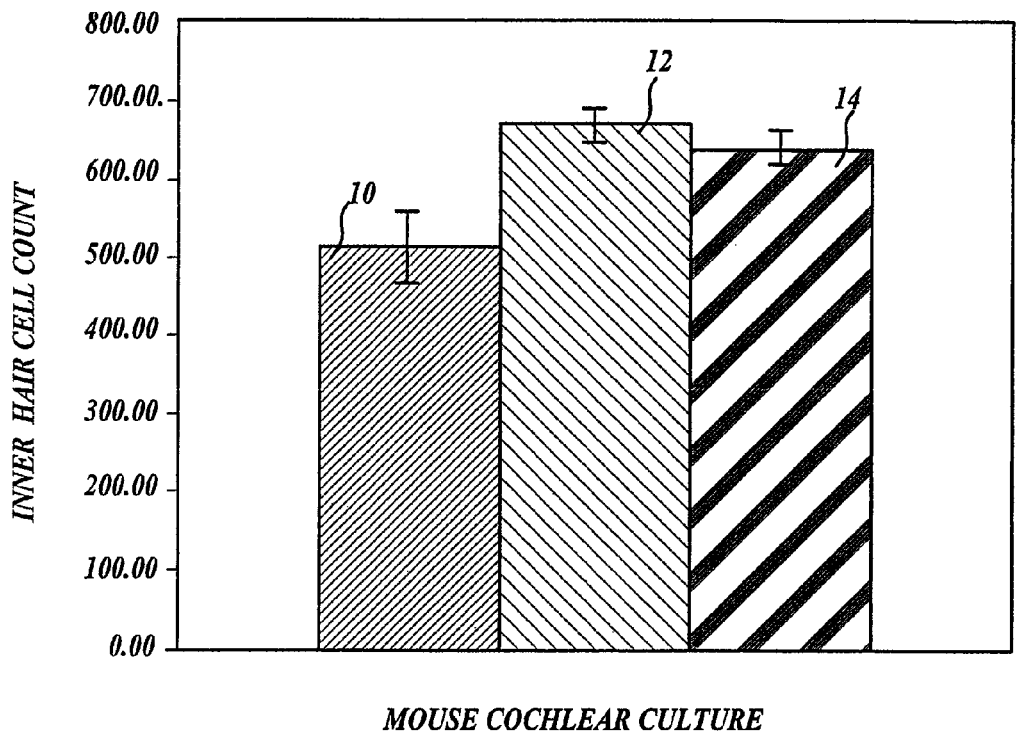
FIG. 7 shows a graph showing the number of inner ear hair cells in rat cochlea that were cultured, in vitro, in the presence of 43 µM cisplatin (10), or 43 µM cisplatin plus 47 µM Ebselen (12), or 47 µM Ebselen (14).

The explants were then harvested, fixed, and stained with calbindin (which detects hair cells) and DAPI (4',6-Diamindino-2-phenylindole; for detection of nuclear DNA). FIG. 7 shows the number of inner ear hair cells in mice cochlea that were cultured, in vitro, in the presence of 43 µM cisplatin (10), or 43 µM cisplatin plus 47 µM Ebselen (12), or 47 µM Ebselen (14). The data set forth in FIG. 7 shows that Ebselen protects inner ear hair cells from damage by cisplatin in vitro.

The concentrations of cisplatin and Ebselen used in the experiments described in this Example are the same concentrations of cisplatin and Ebselen that were used in the cell culture assays described in Example 1. Thus, the experiments reported in Example 1 and Example 2 together show that, at the concentration utilized in these experiments, Ebselen does not protect NuTu-19 ovarian cancer tumor cells from the toxic effects of cisplatin, but does protect inner ear hair cells from the toxic effects of cisplatin.

EXAMPLE 3

This Example shows that Ebselen, and the combination of Ebselen and allopurinol, protect rat inner ear hair cells from damage by cisplatin in vivo.

Auditory Evoked Brainstem Response (ABR) was used to assess hearing in rats before and after exposure to cisplatin and chemoprotectants. Ebselen or DMSO (control vehicle) were introduced intraperitoneally into rats one hour before intraperitoneal administration of cisplatin at a dosage of 16 mg/kg body weight. Seventy two hours after delivery of cisplatin, ABR data were collected, animals were sacrificed, cochleae were collected, dissected, stained with FITC-phalloidin (to detect F-Actin in hair cells), and DAPI (to detect nuclear DNA).

Figure 8:
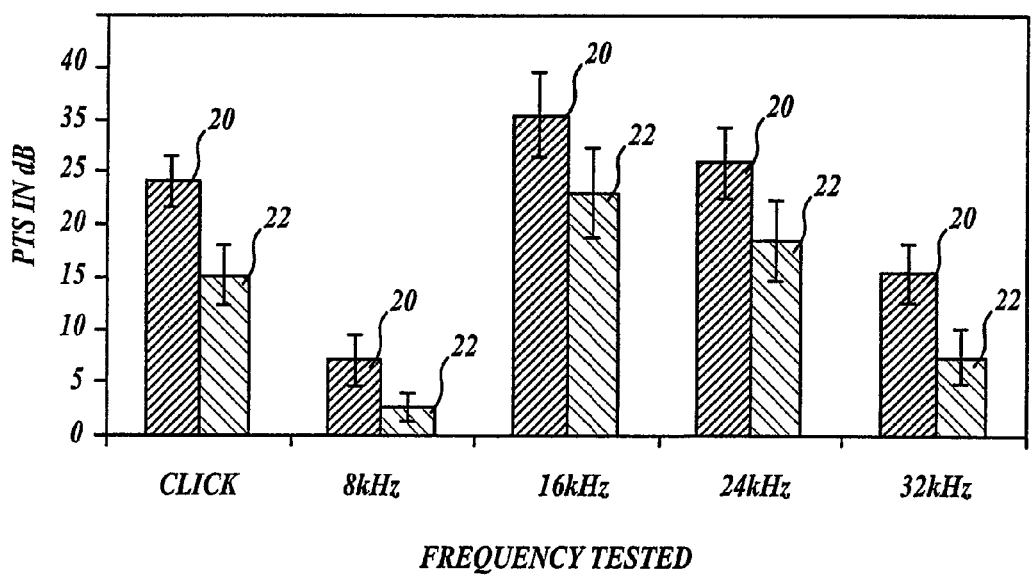
FIG. 8 shows the permanent threshold shift (PTS) in hearing at 8 kHz, 16 kHz, 24 kHz and 32 kHz of rats treated with saline and DMSO (vehicle control)(20), or with cisplatin (at a dosage of 16 mg/kg body weight) in the presence of Ebselen (at a dosage of 16 mg/kg body weight)(22). Ten cochlea were tested per treatment.

FIG. 8 shows the permanent threshold shift (PTS) in hearing, at 8 kHz, 16 kHz, 24 kHz and 32 kHz, of rats treated with cisplatin (at a dosage of 16 mg/kg body weight) in the presence of Ebselen (at a dosage of 16 mg/kg body weight)(22), or in the presence of saline and DMSO (control)(20). Ten cochlea were tested per treatment. The PTS is a measure of hearing loss. The data presented in FIG. 8 show that the PTS is less (i.e., there is less hearing loss) in rats treated with the combination of Ebselen and cisplatin, compared to rats treated with cisplatin without Ebselen.

Figure 9:
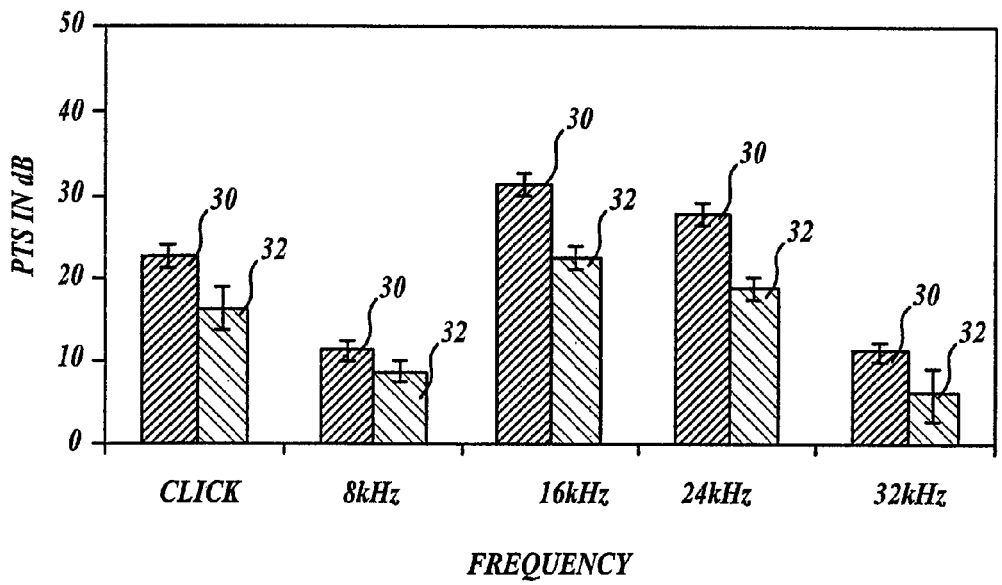
FIG. 9 shows the permanent threshold shift (PTS) in hearing at 8 kHz, 16 kHz, 24 kHz and 32 kHz of rats treated with cisplatin (at a dosage of 16 mg/kg body weight) in the presence of allopurinol (at a dosage of 16 mg/kg body weight) (30), or in the presence of the combination of allopurinol (at a dosage of 8 mg/kg body weight) and Ebselen (at a dosage of 8 mg/kg body weight)(32). Four cochlea were tested per treatment.

FIG. 9 shows the permanent threshold shift (PTS) in hearing, at 8 kHz, 16 kHz, 24 kHz and 32 kHz, of rats treated with cisplatin (at a dosage of 16 mg/kg body weight) in the presence of allopurinol (at a dosage of 16 mg/kg body weight) (30), or in the presence of the combination of allopurinol (at a dosage of 8 mg/kg body weight) and Ebselen (at a dosage of 8 mg/kg body weight)(32). Four cochlea were tested per treatment. The data presented in FIG. 9 show that the PTS is less in rats treated with the combination of Ebselen and allopurinol, compared to rats treated with allopurinol without Ebselen.

Figure 10A:
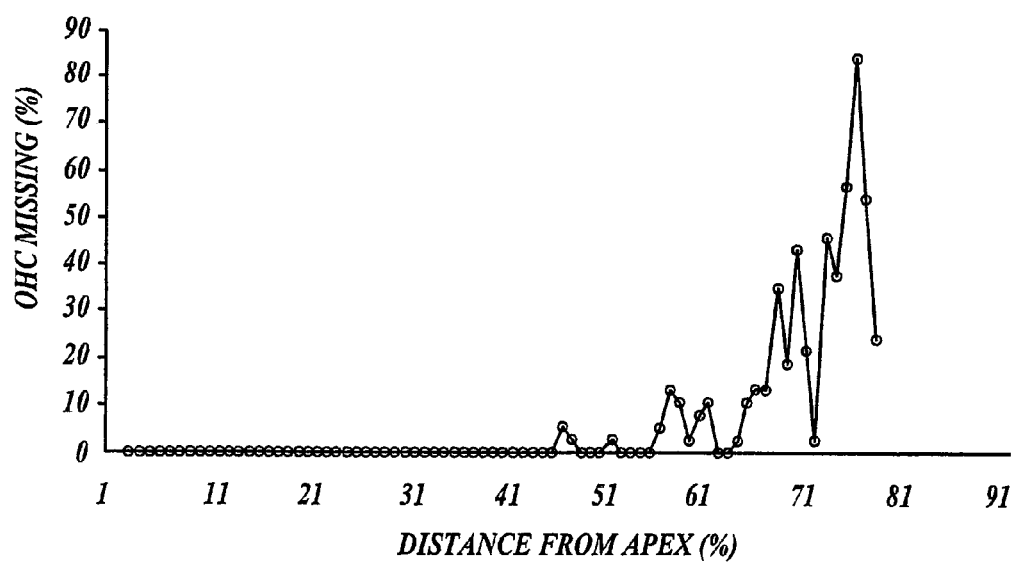
FIG. 10A shows the percentage of missing cochlear outer hair cells plotted against the distance from the apex of the cochlea in the left cochlea of a rat treated with the combination of cisplatin, saline and DMSO.
Figure 10B:
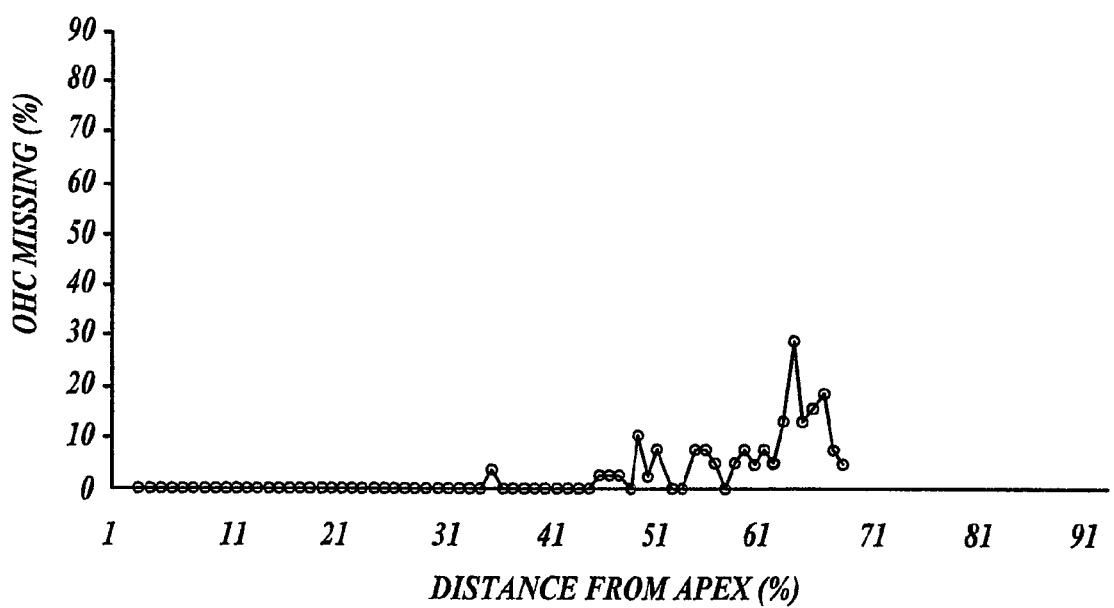
FIG. 10B shows the percentage of missing cochlear outer hair cells plotted against the distance from the apex of the cochlea in the left cochlea of a rat treated with the combination of cisplatin and Ebselen.

Additionally, cochleae were excised from rats treated with the combination of cisplatin and Ebselen as described in this Example. Cochleae were also excised from rats treated with cisplatin and saline and DMSO (control). The number of outer auditory hair cells in the excised cochlea were counted at intervals of 0.1 mm along the cochlea. Representative results from a control rat and a treated rat are shown in FIG. 10A and FIG. 10B, respectively. The data presented in FIG. 10A and FIG. 10B show that the percentage of outer hair cells missing in cochleae from rats treated with the combination of cisplatin and Ebselen is less than the percentage of outer hair cells missing in cochleae from rats treated with cisplatin, but not with Ebselen.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of ameliorating at least one adverse effect of a platinum-containing chemotherapeutic agent, the method comprising the step of administering to a subject undergoing chemotherapy treatment with a platinum-containing chemotherapeutic agent an amount of allopurinol, and an amount of 2-phenyl-1,2-benzoisoselenazol-3(2H)-one, wherein the at least one adverse effect is nephrotoxicity, myelosuppression, or a combination thereof.

2. A method of claim 1, wherein said allopurinol is administered in an amount of from 10 to 2400 mg/day, and said 2-phenyl-1,2-benzoisoselenazol-3(2H)-one is administered in an amount of from 5 to 5000 mg/day.

3. A method of claim 1, wherein the at least one adverse effect is nephrotoxicity.

4. A method of claim 1, wherein the at least one adverse effect is myelosuppression.

5. A method of claim 1, wherein the platinum-containing chemotherapeutic agent is selected from the group consisting of cisplatin, carboplatin, and oxaliplatin.

6. A method of claim 1, wherein the platinum-containing chemotherapeutic agent is cisplatin.

* * * * *